US011147628B2

(12) United States Patent
Zarkh

(10) Patent No.: US 11,147,628 B2
(45) Date of Patent: Oct. 19, 2021

(54) UPDATING AN INDICATION OF A LUMEN LOCATION

(71) Applicant: SYNC-RX, LTD, Netanya (IL)

(72) Inventor: Michael Zarkh, Qiryat Ono (IL)

(73) Assignee: SYNC-RX, LTD, Netanya (IL)

( * ) Notice: Subject to any disclaimer, the term of this patent is extended or adjusted under 35 U.S.C. 154(b) by 491 days.

(21) Appl. No.: 15/630,596

(22) Filed: Jun. 22, 2017

(65) Prior Publication Data

US 2017/0367769 A1    Dec. 28, 2017

Related U.S. Application Data

(60) Provisional application No. 62/353,197, filed on Jun. 22, 2016.

(51) Int. Cl.
*A61B 34/20*    (2016.01)
*A61B 6/00*    (2006.01)
(Continued)

(52) U.S. Cl.
CPC ............ *A61B 34/20* (2016.02); *A61B 5/0084* (2013.01); *A61B 5/7207* (2013.01); *A61B 6/12* (2013.01);
(Continued)

(58) Field of Classification Search
CPC .... A61B 2034/2063; A61B 2034/2065; A61B 34/20; A61B 6/463; A61B 6/487; A61B 6/5247; A61B 6/547; A61B 8/12; A61B 8/461; A61B 8/463; A61B 8/5261; A61B 6/481; A61B 8/0891; A61B 5/7207; A61B 6/461; A61B 6/4417; A61B 6/507; A61B 5/0084; A61B 6/504; A61B 8/0841; A61B 6/484; A61B 6/12; A61B 90/37; A61B 8/5223; A61B 8/5284; A61B 8/06;
(Continued)

(56) References Cited

U.S. PATENT DOCUMENTS 6,192,144 B1 *    2/2001    Holz ...................... G01R 33/28
                                                              382/131
6,493,575 B1    12/2002    Kesten
(Continued)

FOREIGN PATENT DOCUMENTS

WO    2008107905    9/2008
WO    2009153794    12/2009
(Continued)

*Primary Examiner* — Hien N Nguyen

(57) ABSTRACT

Apparatus and methods are described including an endoluminal device configured to move along a portion of a lumen of a subject's body, an extraluminal imaging device, and at least one computer processor. While the endoluminal device moves along the portion of the lumen, a display displays an extraluminal image of the lumen in which a first indication of a location of the lumen is shown. The extraluminal imaging device acquires a sequence of extraluminal images of the endoluminal device moving along the portion of the lumen. The indication of the location of the lumen that is displayed is updated based upon the acquired sequence of extraluminal images, and the acquired sequence of images is displayed with the updated indication of the location of the lumen overlaid upon the images. Other applications are also described.

12 Claims, 4 Drawing Sheets

(51) Int. Cl.
*G06T 7/33* (2017.01)
*A61B 5/00* (2006.01)
*A61B 8/00* (2006.01)
*A61B 8/08* (2006.01)
*A61B 90/00* (2016.01)
*A61B 6/12* (2006.01)
*A61B 8/12* (2006.01)
*A61B 8/06* (2006.01)

(52) U.S. Cl.
CPC ............ *A61B 6/4417* (2013.01); *A61B 6/461* (2013.01); *A61B 6/463* (2013.01); *A61B 6/481* (2013.01); *A61B 6/484* (2013.01); *A61B 6/487* (2013.01); *A61B 6/504* (2013.01); *A61B 6/507* (2013.01); *A61B 6/5247* (2013.01); *A61B 8/0841* (2013.01); *A61B 8/0891* (2013.01); *A61B 8/12* (2013.01); *A61B 8/461* (2013.01); *A61B 8/463* (2013.01); *A61B 8/5261* (2013.01); *A61B 90/37* (2016.02); *G06T 7/337* (2017.01); *A61B 6/547* (2013.01); *A61B 8/06* (2013.01); *A61B 8/5223* (2013.01); *A61B 8/5284* (2013.01); *A61B 2034/2063* (2016.02); *A61B 2034/2065* (2016.02); *A61B 2090/365* (2016.02); *A61B 2090/374* (2016.02); *A61B 2090/3762* (2016.02); *A61B 2090/3782* (2016.02); *G06T 2207/10016* (2013.01); *G06T 2207/10121* (2013.01); *G06T 2207/10132* (2013.01); *G06T 2207/30021* (2013.01); *G06T 2207/30101* (2013.01)

(58) Field of Classification Search
CPC .... A61B 2090/3782; A61B 2090/3762; A61B 2090/374; A61B 2090/365; G06T 7/337; G06T 2207/10132; G06T 2207/30021; G06T 2207/10016; G06T 2207/10121; G06T 2207/30101
See application file for complete search history.

(56) References Cited

U.S. PATENT DOCUMENTS

| | | |
|---|---|---|
| 8,700,130 B2 | 4/2014 | Iddan et al. |
| 8,781,193 B2 | 7/2014 | Steinberg et al. |
| 2003/0099389 A1* | 5/2003 | Zeng .................... G06T 7/0012 382/131 |
| 2006/0257006 A1 | 11/2006 | Bredno |
| 2008/0221440 A1 | 9/2008 | Iddan et al. |
| 2008/0275335 A1 | 11/2008 | Zhang |
| 2009/0163800 A1 | 6/2009 | Xu |
| 2010/0222671 A1 | 9/2010 | Cohen et al. |
| 2012/0004537 A1* | 1/2012 | Tolkowsky ............ A61B 5/066 600/424 |
| 2012/0230565 A1 | 9/2012 | Steinberg et al. |
| 2014/0094691 A1* | 4/2014 | Steinberg ............ A61B 5/7425 600/424 |
| 2014/0121513 A1 | 5/2014 | Tolkowsky et al. |
| 2014/0140597 A1 | 5/2014 | Barzelay et al. |
| 2014/0276684 A1 | 9/2014 | Huennekens |
| 2015/0313563 A1 | 11/2015 | Kelm |
| 2016/0287278 A1* | 10/2016 | Stigall ................. A61B 5/0084 |
| 2016/0321495 A1* | 11/2016 | Chukka ................ G06T 7/0014 |

FOREIGN PATENT DOCUMENTS

| | | |
|---|---|---|
| WO | 2010058398 | 5/2010 |
| WO | 2011145094 A2 | 11/2011 |
| WO | 2012014212 A2 | 2/2012 |
| WO | 20120176191 A1 | 12/2012 |
| WO | 2013175472 | 11/2013 |
| WO | 2014002095 A2 | 1/2014 |
| WO | 2014020495 A1 | 2/2014 |
| WO | 20150155770 A1 | 10/2015 |
| WO | 2015173821 | 11/2015 |

* cited by examiner

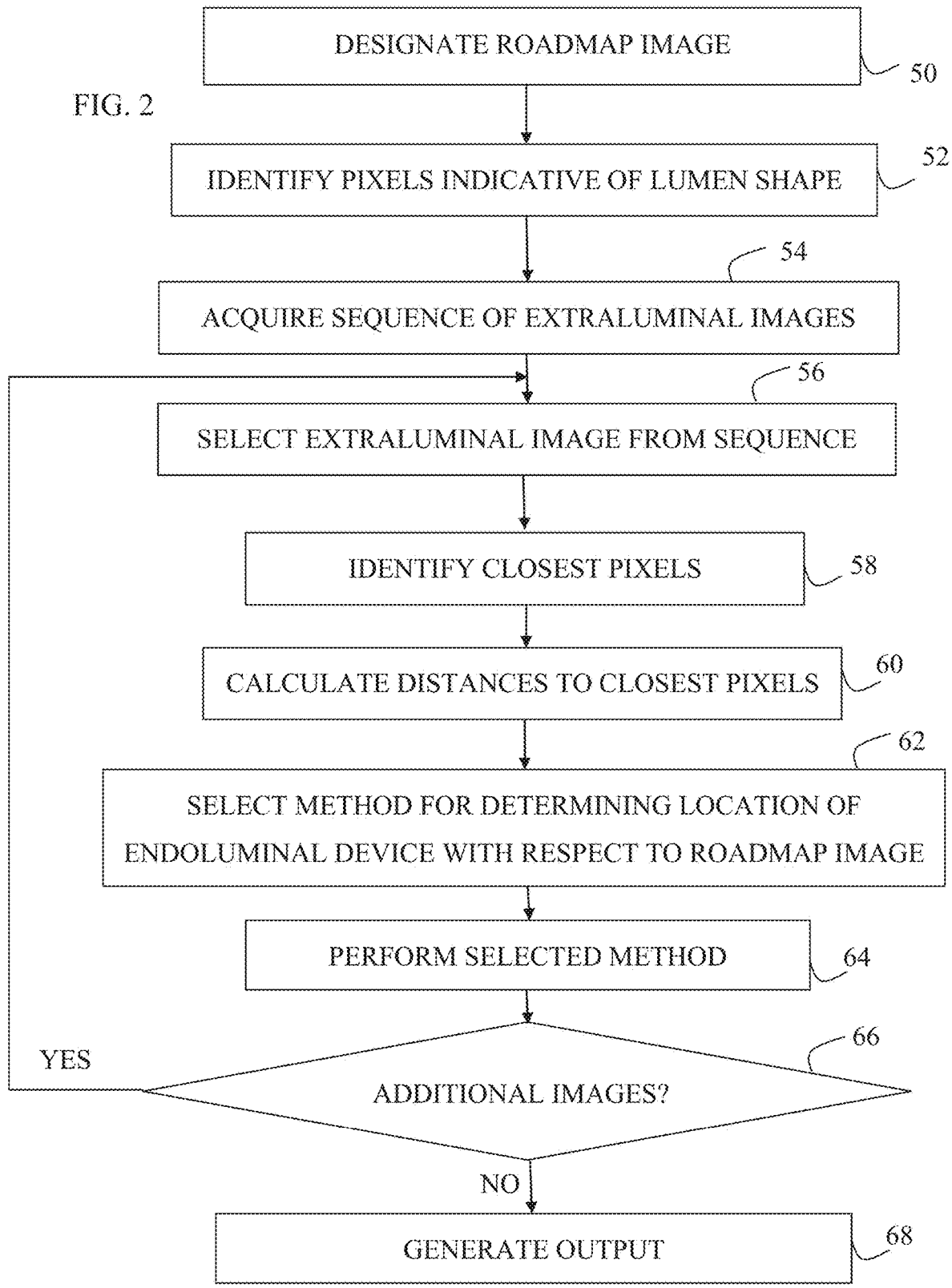

FIG. 4
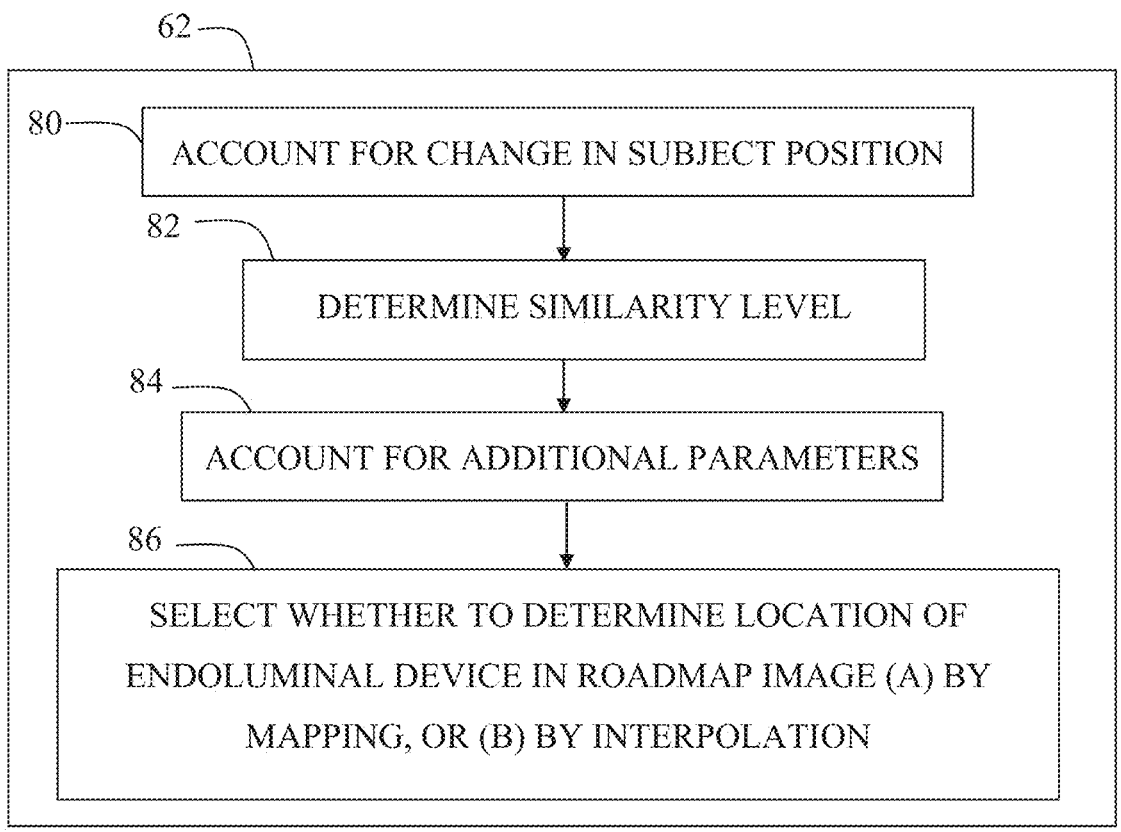
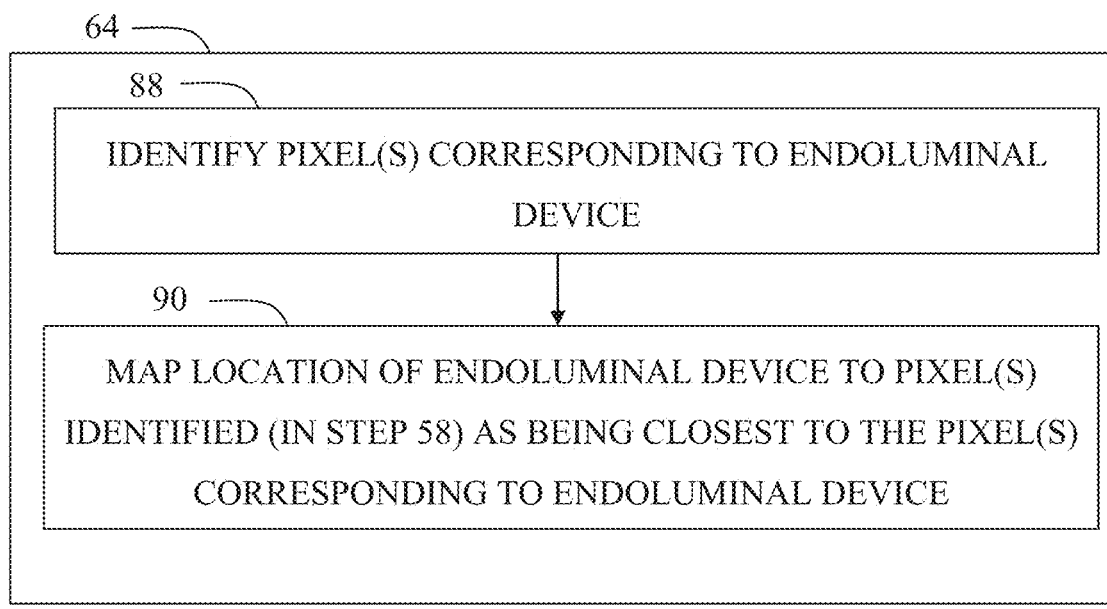

UPDATING AN INDICATION OF A LUMEN LOCATION

CROSS-REFERENCE TO PRIOR APPLICATION

This application claims the benefit of U.S. Provisional Patent Application No. 62/353,197, filed Jun. 22, 2016 which is hereby incorporated by reference herein.

FIELD OF EMBODIMENTS OF THE INVENTION

Some applications of the present invention generally relate to automatic image processing. Specifically, some applications of the present invention relate to medical imaging and analysis of such images.

BACKGROUND

Vascular catheterizations, such as coronary catheterizations, are frequently performed medical interventions. Such interventions are typically performed in order to diagnose the blood vessels for potential disease, and/or to treat diseased blood vessels. Typically, in order to enable observation of blood vessels, the catheterization is performed under extraluminal imaging. Additionally, for some procedures, an endoluminal data-acquisition device is used to perform endoluminal imaging and/or measurements. The extraluminal imaging and, where applicable, the endoluminal data are typically evaluated by the medical staff in combination with one another in the course of the intervention, as well as post-procedurally.

SUMMARY OF EMBODIMENTS

In accordance with some applications of the present invention, an extraluminal image of a lumen of a subject's body is displayed, in which an indication of a location of the lumen is shown, while an endoluminal device (such as an endoluminal data-acquisition device) moves along a portion of the lumen. A sequence of extraluminal images of the endoluminal device moving along the portion of the lumen is acquired, using an extraluminal imaging device. The indication of the location of the lumen that is displayed is updated, based upon the acquired sequence of extraluminal images of the endoluminal device moving along the portion of the lumen. The sequence of images of the endoluminal device moving along the portion of the lumen is displayed with the updated indication of the location of the lumen overlaid upon the images.

The present invention will be more fully understood from the following detailed description of embodiments thereof, taken together with the drawings, in which:

BRIEF DESCRIPTION OF THE DRAWINGS

FIG. 2 is a flowchart showing steps of a procedure that is used to map images belonging to a sequence of extraluminal images of a lumen to a roadmap image of the lumen, in accordance with some applications of the present invention;

FIG. 4 is a flowchart showing sub-steps of the procedure shown in FIG. 2 that are performed, in accordance with some applications of the present invention.

DETAILED DESCRIPTION OF EMBODIMENTS

Figure 1:
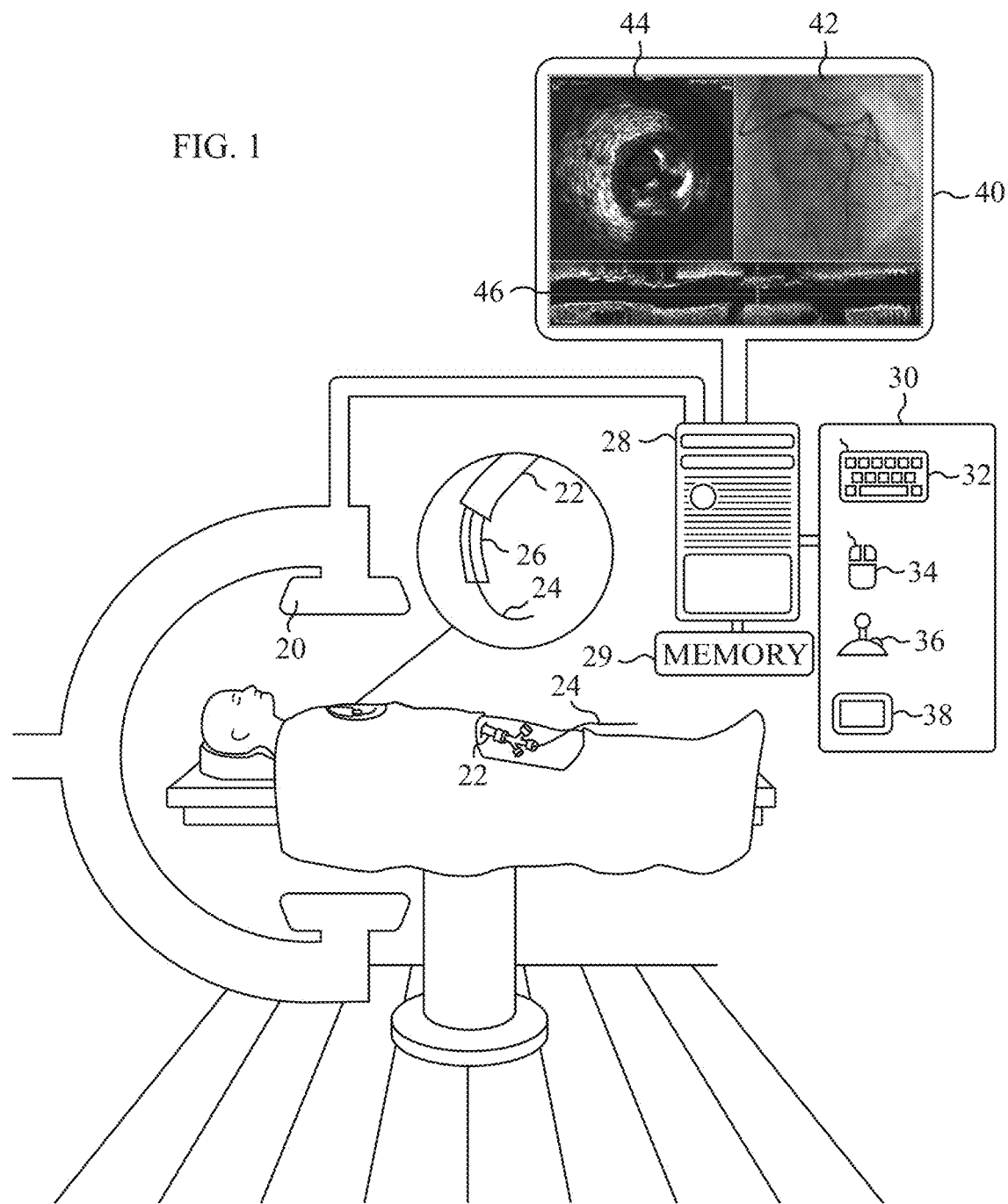
FIG. 1 is a schematic illustration of apparatus that is used in a catheterization laboratory, in accordance with some applications of the present invention.

Reference is now made to FIG. 1, which is a schematic illustration of apparatus that is used in a catheterization laboratory, in accordance with some applications of the present invention. Typically, a subject is imaged using an extraluminal imaging device (i.e., an extraluminal image-acquisition device) 20, which may include a fluoroscope that acquires fluoroscopic images under regular mode (in the absence of contrast agent in the blood vessels of the subject that are being imaged) and/or under angiographic mode (while there is a presence of contrast agent in the blood vessels of the subject that are being imaged). For some applications, the imaging device performs fluoroscopy, CT, MR, PET, SPECT, ultrasound, or any combination thereof.

FIG. 1 additionally shows a guide catheter 22 that has been inserted into a blood vessel of the subject (e.g., a coronary artery of the subject) over a guidewire 24. An endoluminal device 26 (which is typically an endoluminal medical device) has been inserted into the subject's blood vessel (e.g., the subject's coronary artery) through the guide catheter and over the guidewire. For some applications (e.g., for applications in which the endoluminal device is an iFR probe), the endoluminal device is inserted into the vessel in the absence of guidewire 24.

For some applications, endoluminal medical device 26 includes an endoluminal data-acquisition device that is configured to acquire data (e.g., functional data or images) from inside the subject's blood vessels. For some applications, the endoluminal data-acquisition device is an imaging probe, such as an intravascular ultrasound (IVUS) probe. For some applications, the endoluminal data-acquisition device includes a probe that is configured to acquire data in a form other than images, such as a Fractional Flow Reserve (FFR) probe, and/or an instantaneous wave-free ratio (iFR) probe. For example, the data may include data related to pressure, flow, temperature, electrical activity, oxygenation, biochemical composition, or any combination thereof.

A computer processor 28 typically receives and processes images (e.g., extraluminal images or endoluminal images). The computer processor communicates with a memory 29. Via a user interface 30, a user (e.g., a physician and/or a catheterization laboratory technician) sends instructions to the computer processor. For some applications, the user interface includes a keyboard 32, a mouse 34, a joystick 36, a touchscreen device 38 (such as a smartphone or a tablet computer), a touchpad, a trackball, a voice-command interface, and/or other types of user interfaces that are known in the art. Typically, the computer processor generates an output using an output device 40. Further typically, the output device includes a display, such as a monitor (as shown in FIG. 1), and the output includes an output that is displayed on the display. For some applications, the display includes a head-up display and/or a head-mounted display, such as Google Glass®. For some applications, the processor generates an output on a different type of visual, text, graphics, tactile, audio, and/or video output device, e.g., speakers, headphones, a smartphone, or a tablet computer. For some applications, user interface 30 acts as both an input device and an output device. For some applications, the processor generates an output on a computer-readable medium (e.g., a non-transitory computer-readable medium), such as a disk or a portable USB drive.

It is noted that, for some applications, more than one computer processor is used to perform the functions described herein as being performed by computer processor 28. For some applications, more than one extraluminal imaging device is used with computer processor 28. For example, a first extraluminal imaging device may be used to acquire a first set of extraluminal images, and a second extraluminal imaging device may be used to acquire a second set of extraluminal images.

For some applications, output device 40 is a display that is configured to display an extraluminal image 42 of a blood vessel (e.g., a fluoroscopic image), an endoluminal image of a blood vessel 44 (e.g., an IVUS image), and or a stack 46 of cross-sections of endoluminal images (e.g., a stack of IVUS images).

Reference is now made to FIG. 2, which is a flowchart showing steps of a procedure that is used to map images belonging to a sequence of extraluminal images of a lumen to a roadmap image of the lumen, in accordance with some applications of the present invention. Reference is also made to FIGS. 3A-D, which are schematic illustrations of images of a lumen (e.g., an artery) 70 of a subject, in accordance with some applications of the present invention.

In a first step 50 of the procedure, processor 28 designates a first extraluminal image as a roadmap image. Typically, a first set of extraluminal images is acquired, and the processor designates at least one of the first set of images as the roadmap image, using one or more of the algorithms described herein. For example, extraluminal imaging device 20 (FIG. 1) may be used to acquire a first set of extraluminal images of a blood vessel (e.g., a coronary artery) of the subject. In accordance with respective applications, the first set of extraluminal images is acquired in a presence of contrast agent within the lumen, or in an absence of contrast agent within the lumen. Typically, at least one of the first set of images is designated as the roadmap image in accordance with techniques described in US 2014/0094691 to Steinberg, and/or WO 13/175472 to Steinberg, both of which applications are incorporated herein by reference. For example, the image may be selected based upon the following criteria: (a) the image is acquired at a desired cardiac phase (typically end diastole) and/or (b) in the image, contrast agent highlights the lumen. For procedures in which the techniques described herein are performed on a subject's coronary arteries, an image may be selected from the set of images based upon visibility of at least a portion of the coronary arteries in the set of images. For some applications, an angiogram with the greatest visibility of coronary arteries is selected, with such selection typically being automatic. The greatest visibility is typically determined based upon the greatest total number of arteries observed, the greatest number of image pixels attributed to an artery, and/or the greatest image contrast in the appearance of specific arteries. For some applications, an extraluminal image that is based upon a plurality of extraluminal images (e.g., an image that is based upon averaging a plurality of images) is selected and designated as the roadmap image. For some applications, the roadmap image is designated at least partially in response to a user input.

Figure 3A:
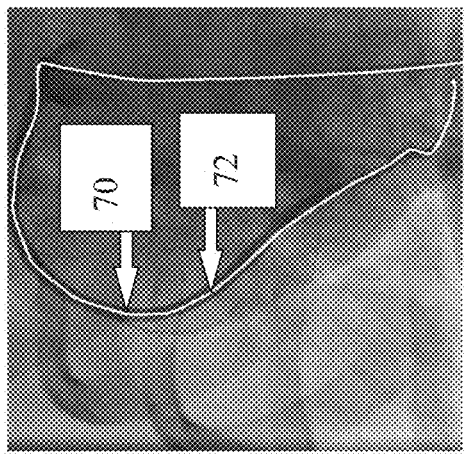
FIGS. 3A, 3B, 3C, and 3D are schematic illustrations of images of a lumen (e.g., an artery) of a subject, in accordance with some applications of the present invention.

FIG. 3A shows an illustrative example of an image of a subject's arteries that has been designated as a roadmap image, in accordance with some applications of the present invention. It may be observed that, in the roadmap image, an artery 70 is highlighted with contrast agent.

Referring again to FIG. 2, in step 52, processor 28 identifies a set of pixels within the roadmap image as being indicative of a shape of the lumen within the roadmap image, typically using one or more of the algorithms described herein.

Typically, the roadmap image is an image in which the lumen is visible. For example, the roadmap image may be an angiographic image acquired in the presence of contrast agent within the lumen. For some such applications, the computer processor identifies pixels as corresponding to the shape of the lumen within the roadmap image, based upon the visible lumen within the image. Alternatively or additionally, the processor identifies visible features of one or more tools that are disposed inside the lumen within the roadmap image. For example, the processor may identify one or more radiopaque features of tools (such as radiopaque markers, and/or a radiopaque tip of a guidewire or guide catheter) that are disposed inside the lumen. Since the tools are disposed inside the lumen, the arrangement of the visible features of the tools provides an indication of the shape of the lumen, and thereby provides an indication of pixels within the roadmap image that are indicative of a shape of the lumen.

For some applications, the lumen is visible within the roadmap image, and the computer processor designates a roadmap pathway based upon the shape of the lumen within the roadmap image. Typically, the roadmap pathway is designated in accordance with the techniques described in US 2014/0094691 to Steinberg and/or WO 13/175472 to Steinberg, both of which applications are incorporated herein by reference. For some applications, the roadmap pathway is designated in response to a manual user input, and/or automatically. For example, the pathway may be designated by the user indicating some points along the path and the processor completing the path, based upon the manually indicated points. Typically, the pixels within the roadmap pathway are identified as being indicative of the shape of the lumen within the roadmap image.

For some applications, the roadmap pathway is at least partially determined by determining the center-line of the lumen. For example, the center-line of the lumen may be determined using techniques for determining the center-line of a lumen described in US 2012/0230565, WO 10/058398, WO 12/014212, and/or US 2012/0004537, all of which applications are incorporated herein by reference.

For some applications (e.g., if the roadmap image is acquired in the absence of contrast agent within the lumen), the roadmap pathway is designated by identifying visible features of one or more tools that are disposed inside the lumen within the roadmap image. As described hereinabove, since the tools are disposed inside the lumen, the arrangement of the visible features of the tools provides an indication of the shape of the lumen. Therefore, for some applications, a roadmap pathway that is indicative of the shape of the lumen is designated based upon identified visible features.

Figure 3B:
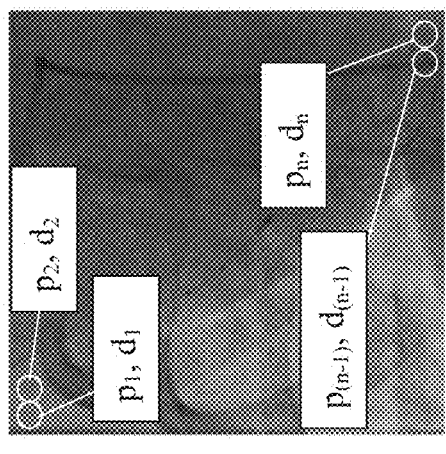

FIG. 3B shows the roadmap image of FIG. 3A, with a roadmap pathway 72 having been designated within artery 70. It is noted that, although, in FIG. 3B, pathway 72 is displayed within the roadmap image, for some applications, the roadmap pathway is designated without the path actually being displayed on a display. In general, it is noted that intermediate steps of the algorithm shown in FIG. 2 (such as identifying a set of pixels within the roadmap image as being indicative of a shape of the lumen within the roadmap image (step 52), and/or additional steps described hereinbelow), may be performed without any output being generated that directly corresponds to these intermediate steps. Rather, such steps may be performed algorithmically by the processor.

Referring again to FIG. 2, in step 54, an extraluminal imaging device (e.g., extraluminal imaging device 20, shown in FIG. 1) acquires a sequence of extraluminal images (hereinafter "the sequence of extraluminal images"). Typically, the sequence of extraluminal images is a sequence of fluoroscopic images, at least some of which are acquired in an absence of contrast agent within the lumen. Further typically, the sequence of extraluminal images is acquired while an endoluminal device (e.g., an endoluminal data-acquisition device, or a therapeutic endoluminal device) is being moved along a portion of the lumen.

Figure 3C:
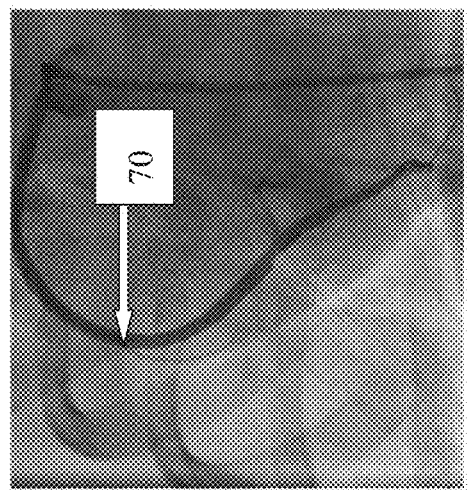

FIG. 3C shows an example of an extraluminal image acquired in an absence of contrast agent within the lumen. It may be observed that, in FIG. 3C, the lumen itself is not highlighted with contrast agent, although there are darkened portions of the image corresponding to radiopaque objects that are disposed within the lumen, and that are therefore visible within the image.

In step 56, one of the images belonging to the sequence of extraluminal images is selected. In step 58, within the selected image, for each of at least some of the pixels within the image, the closest pixel to the pixel from the set of pixels within the roadmap image is identified. In step 60, the computer processor, determines the distances between the pixels belonging to the selected extraluminal image, and the pixel from the set of pixels within the roadmap image that was determined to be closest to the pixel in step 58.

For some applications, the computer processor performs steps 58 and 60 by identifying pixels that correspond to visible features within the image, and performing steps 58 and 60 with respect to the identified pixels. Typically, at least some of the visible features correspond to features that are disposed within the lumen, such as radiopaque markers of the endoluminal device, and/or a radiopaque tip of a guidewire or guide catheter.

Reference is made to FIG. 3C, which shows an extraluminal image, in which steps 58 and 60 are schematically shown to have been performed with respect to pixels corresponding to visible features within the image. As indicated schematically, for each of the identified pixels, a closest pixel ($p_x$) belonging to the set of pixels within the roadmap image has been identified, and the distance ($d_x$) between the pixel and the identified closest pixel has been calculated.

For some applications, steps 58 and 60 are performed in the following manner. Initially, an image is selected as a "master image". For example, the master image may be one of the extraluminal images from the sequence of extraluminal images, or may be a blank image that is of a similar size to the images belonging to the sequence of extraluminal images. For the master image, a function is determined that describes for each of a plurality of pixels within the image, (a) the closest pixel to the pixel from the set of pixels within the roadmap image, and (b) a distance between the pixel and the pixel identified as the closest pixel. For example, the function may describe the aforementioned parameters with respect to all of the pixels within the image, or within all of the pixels within the image, apart from pixels that are disposed within pre-defined margins of the image. Subsequently, for images within the sequence of extraluminal images, steps 58 and 60 are performed by applying the function determined with respect to the master image to selected pixels within each of the images.

Figure 3D:
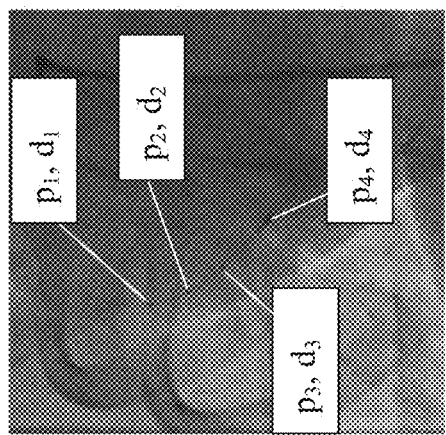

For example, FIG. 3D schematically illustrates a master image, in which, for pixels starting in the top left of the image through to the bottom right of the image, for each pixel the closest pixel ($p_x$) to the pixel from the set of pixels within the roadmap image has been identified, and a distance ($d_x$) between the pixel and the pixel identified as the closest pixel has been calculated.

In step 62, at least partially in response to steps 58 and 60, computer processor 28 selects a method for identifying, with respect to the roadmap image, a location at which the endoluminal device was located at a time at which the image belonging to the sequence of extraluminal images was acquired.

Reference is now made to FIG. 4, which is a flowchart showing sub-steps of the procedure shown in FIG. 2 that are performed, in accordance with some applications of the present invention. For some applications, step 62 is performed in the following manner. In a sub-step 82, the computer processor determines a level of similarity between the image belonging to the sequence of images, and the roadmap image. For example, the computer processor may determine the level of similarity based upon the distances between pixels in the images belonging to the sequence of extraluminal images, and the closest pixels to those pixels from the set of pixels within the roadmap image (as identified in Step 60). The computer processor may determine the level of similarity by considering a sum of the distances, an average of the distances (e.g., a mean of the distances), and/or based on additional factors. For example, the computer processor may determine a measure of a transformation (e.g., stretching, rotation, shrinking, etc.) that needs to be applied to the extraluminal image in order to best fit the extraluminal image to the roadmap image, and the level of similarity may be determined based upon the measure of transformation.

Typically, between the acquisition of the roadmap image, and the acquisitions of the extraluminal images belonging to the sequence of extraluminal images, the lumen has undergone changes in location and shape (e.g., due to the subject's respiratory cycle, due to the subject's cardiac cycle, due to other movement of the subject, and/or due to the devices within the lumen having moved the lumen). Typically, the level of similarity that is determined in sub-step 82 is indicative of the level of similarity between the shape of the lumen in the roadmap image and the shape of the lumen in the image belonging to the sequence of extraluminal images.

It is noted that the subject may undergo a change in position between acquisition of the roadmap image and acquisition of the sequence of extraluminal images. For some applications, as a preliminary step to sub-step 82, the computer processor determines the change in position of the subject's body between the acquisition of the roadmap image and the acquisition of the sequence of extraluminal images, and, in sub-step 80, the computer processor accounts for the change in position in performing steps 58 and 60 of FIG. 2.

For some applications, changes in the position of the subject's body are measured using external sensors, such as electromagnetic location sensors that are attached to the subject's body. Alternatively or additionally, locations at which visible features were imaged within the sequence of extraluminal images are identified by the computer processor. The computer processor defines a set of locations at which visible features were located over the course of the sequence of extraluminal images, based upon the identified locations. For example, a combined image may be generated in which the identified locations form an integrated set of locations, by overlaying, upon each other, the locations of the visible features identified in each of the images belonging to the sequence of extraluminal images. The computer processor then estimates a location of the lumen during the acquisition of the sequence of extraluminal images based upon the set of locations. Typically, a curve that defines the set of locations is identified and the curve is identified as a centerline of the lumen. For example, a center-line of the set of locations may be identified as the center-line of the lumen. The change in the position in the subject's body is determined by determining a difference between the location of the lumen within the roadmap image (e.g., the location of the roadmap pathway within the roadmap image), and the location of the determined curve. The difference between the location of the lumen within the roadmap image, and the location of the determined curve is indicative of the change in the position of the subject's body. By performing sub-step 80 as a preliminary step toward sub-step 82, the level of similarity of an image belonging to the sequence of extraluminal images to the roadmap image is determined by the processor, while accounting for the change in the subject's position.

For some applications, additional parameters are accounted for in selecting the method by which to determine the location of the endoluminal device at the time that the image was acquired, with respect to the roadmap image (sub-step 84 of FIG. 4). For example, in selecting the method, the computer processor may account for parameters such as maintaining a given separation between given features (e.g., between pairs of markers), the velocity of the endoluminal device, movement continuity, and quality of the mapping of the guide catheter.

It is noted that, as described hereinabove, for some applications, the computer processor estimates a location of the lumen during the acquisition of the sequence of extraluminal images, which is different from the location of the lumen as indicated in the roadmap image. For some applications, in response to estimating the location of the lumen, the computer processor generates an output that is indicative of the location of the lumen during the acquisition of the sequence of extraluminal images, thereby compensating for the change in the location of the lumen since the acquisition of the roadmap image. Alternatively or additionally, the computer processor may generate an output that is indicative of the estimated shift in the lumen location, between the acquisition of the roadmap image and the acquisition of the sequence of extraluminal images.

For example, the computer processor may initially drive the display to display a roadmap image upon which an indication of the location of the lumen is shown (e.g., by indicating the roadmap pathway), and the computer processor may then drive the display to display an updated indication of the location of the lumen (e.g., an updated roadmap pathway), based upon the estimated location of the lumen during the acquisition of the sequence of extraluminal images. Alternatively or additionally, the computer processor may drive the display to display a playback sequence in which movement of the endoluminal device along a portion of the lumen (as imaged in the sequence of extraluminal images) is displayed upon the updated indication of the location of the lumen (e.g., the updated roadmap pathway). For some applications, the computer processor drives the display to simultaneously display a playback sequence in which movement of the endoluminal device (as imaged in the sequence of extraluminal images) is displayed upon the indication of the location of the lumen as derived from the roadmap image (i.e., the original roadmap pathway).

For some applications, the computer processor drives the display to display a plot in which the acquired endoluminal data sets (or derivatives thereof) are plotted against the distance along the vessel lumen at which the data sets were acquired. For some applications, while the computer processor drives the display to display a playback sequence as described above, the computer processor additionally displays an icon on the graph that is indicative of the location of the endoluminal data-acquisition device as is currently being shown in the playback sequence.

Referring again to FIG. 4, at least partially in response to determining the level of similarity between the image belonging to the sequence of extraluminal images, and the roadmap image, a method is selected for identifying, with respect to the roadmap image, a location at which the endoluminal device was located at a time at which the image belonging to the sequence of extraluminal images was acquired. For example, as shown in step 86 of FIG. 4, the level of similarity may be used an input for selecting whether to (a) map the location of the endoluminal device within the image belonging to the sequence of extraluminal images to a corresponding location within the roadmap image, or (b) to determine the location of the endoluminal device at the time that the image was acquired, with respect to the roadmap image, by interpolating between locations of the endoluminal device within the roadmap image at times at which different extraluminal images were acquired.

Referring again to FIG. 2, in step 64, the method selected in step 62 is performed, in order to determine, with respect to the roadmap image, the location of the endoluminal device at the time that the image belonging to the sequence of extraluminal images was acquired. (It is noted that, if the selected method is interpolation, then the selected method may not be performed immediately. Rather, it may be necessary to first determine the locations of the endoluminal device at times that other images belonging to the sequence of extraluminal images were acquired, and to then perform the interpolation based upon those determined positions.)

Referring to FIG. 4, for some applications, in response to selecting (in step 62 and/or in sub-step 86) to map the location of the endoluminal device within the image belonging to the sequence of extraluminal images to a corresponding location within the roadmap image, the computer processor performs the following sub-steps. In sub-step 88, the computer processor identifies one or more pixels within the extraluminal image belonging to the sequence of extraluminal images as corresponding to a portion of the endoluminal device. Subsequently, in sub-step 90, the computer processor maps the pixel(s) corresponding to the portion of the endoluminal device to the pixel(s) that were previously determined as being closest to the pixel(s) from the set of pixels within the roadmap image in step 58.

Referring again to FIG. 2, in step 66, the computer processor determines whether there are additional images belonging to the sequence of extraluminal images with respect to steps 56-64 should be performed. Steps 56-64 are typically performed iteratively with respect to a plurality of the images belonging to the sequence of extraluminal images. Thus, the computer processor determines the location of the endoluminal device with respect to the roadmap image at times corresponding to the acquisitions of a plurality of images belonging to the sequence of extraluminal images, the images having been acquired at respective times during the movement of the endoluminal device through the lumen. Typically, in step 68, processor 28 generates an output on output device 40, in response to steps 56-64 having been performed with respect to a plurality of the images belonging to the sequence of extraluminal images.

For some applications, the processor generates an output indicative of the determined location of the endoluminal device with respect to the roadmap image. For some applications, the output indicative of the determined location of the endoluminal device with respect to the roadmap image is generated by the processor in real-time with respect to acquisition of the image belonging to the sequence of extraluminal images.

Typically, steps 56-64 are performed with respect to a plurality of the images belonging to the sequence of extraluminal images. Thus, a plurality of locations of the endoluminal device, at times at which respective extraluminal images belonging to the sequence of extraluminal images were acquired, are determined, with respect to the roadmap image.

For some applications, the endoluminal device is an endoluminal data-acquisition device that is configured to acquire a plurality of endoluminal data sets from respective locations along the lumen. For example, the endoluminal data-acquisition device may be an endoluminal imaging device configured to acquire a plurality of endoluminal images from respective locations along the lumen. Alternatively or additionally, the endoluminal data-acquisition device may be configured to collect data sets relating to functional characteristics of the lumen (i.e., functional data sets) from respective locations along the lumen. Based upon the locations of the endoluminal device at times of acquisitions of respective extraluminal images with respect to the roadmap image, the processor determines the location at which one or more endoluminal data sets were acquired by the endoluminal data-acquisition device, with respect to the roadmap image.

Typically, computer processor 28 determines which endoluminal data sets were acquired at the same time as respective extraluminal images. For example, a single computer (or two or more computers that are time-synchronized) may operate both the extraluminal imaging and the endoluminal data-acquisition, and the computer may log the times at which extraluminal images and endoluminal data sets were acquired. Or, the processor may determine which endoluminal data sets were acquired at the same time as respective extraluminal images, based upon known frame rates at which the extraluminal images and the endoluminal data sets are acquired. By determining an estimate of where, at the time when the extraluminal image was acquired, the data-acquiring portion of the data-acquisition device (e.g., the endoluminal data-acquisition device head) was disposed with respect to the roadmap image, the processor determines the location of the endoluminal data set that was acquired at the same time as the extraluminal image, with respect to the roadmap image.

Typically when sub-step 86 (FIG. 4) is performed with respect to a plurality of images belonging to the sequence of extraluminal images, the computer processor determines that for a first portion of the images mapping should be used to determine the location of the endoluminal device with respect to the roadmap image, and that for a second portion of the images interpolation should be used to determine the location of the endoluminal device with respect to the roadmap image. Thus, when used with an endoluminal data-acquisition device, typically, locations of a first portion of the endoluminal data sets are determined with respect to the roadmap image via mapping, and locations of a second portion of the endoluminal data sets are determined with respect to the roadmap image via interpolation.

For some applications, processor 28 performs the interpolation with respect to the mapped locations of the endoluminal data sets, such as to determine the locations of the second portion of endoluminal data sets with respect to the roadmap image. For some applications, computer processor 28 additionally uses interpolation to determine, with respect to the roadmap image, the locations of endoluminal data sets that were acquired at times between acquisitions of extraluminal images belonging to the second set of extraluminal images.

For some applications, generally similar techniques to those described in US 2014/0094691 to Steinberg, and/or WO 13/175472 to Steinberg, both of which applications are incorporated herein by reference, are used for performing the interpolation. Typically, the interpolation is performed by optimizing a cost of a trajectory of the endoluminal data-acquisition device, throughout the movement of the endoluminal data-acquisition device with respect to the lumen. The cost includes parameters such as maintaining a given separation between given features (e.g., between pairs of markers), the velocity of the endoluminal data-acquisition device, movement continuity, and quality of the mapping of the guide catheter. The resulting trajectory is smoothed and the result is a floating point model index of endoluminal data-acquisition device locations along the roadmap image.

For some applications, the interpolation is performed by applying parameter estimation techniques to the determined locations of the data-acquiring portion of the endoluminal data-acquisition device along the roadmap image. For example, temporal filtration techniques, and/or outlier removal techniques may be applied to the determined locations of the data-acquiring portion of the endoluminal data-acquisition device along the roadmap pathway.

For some applications, in order to perform the interpolation, at least a portion of the roadmap image (e.g., the roadmap pathway) is first calibrated, e.g., using techniques described hereinabove, and/or in US 2014/0094691 to Steinberg and/or WO 13/175472 to Steinberg, both of which applications are incorporated herein by reference.

For some applications, computer processor 28 calibrates the roadmap image by determining the relationship between the physical dimension of a portion of the lumen and a number of pixels in a portion of the roadmap image that corresponds to the portion of the lumen (e.g., the length in mm along the lumen, per pixel along the roadmap image). It is noted that typically, the calibration factors associated with respective portions of a lumen in an image vary, due to respective portions of the lumen being disposed at respective angles with respect to the extraluminal imaging device, and therefore having respective levels of foreshortening in the roadmap image. Therefore, typically, the computer processor determines a plurality of local calibration factors along the lumen within the roadmap image (e.g., along a roadmap pathway). For some applications, in response to the determined transformation functions, processor determines localized calibration factors along the lumen within the roadmap image, using generally similar techniques to those described in US 2014/0094691 to Steinberg, and/or WO 13/175472 to Steinberg, both of which applications are incorporated herein by reference.

For some applications, in step 68 of FIG. 2, computer processor 28 generates an output, based upon the determined locations within the lumen at which the endoluminal data sets were acquired. For example, the computer processor may generate an endoluminal image stack, and/or the computer processor may generate an indication of the correspondence between an endoluminal data set and the location within the lumen on the roadmap image at which the endoluminal data set was acquired. Alternatively, based upon the determined locations within the lumen at which the endoluminal data sets were acquired, the processor may co-use endoluminal data sets and extraluminal imaging using techniques described herein, and/or as described in US 2012/0004537 to Tolkowsky, US 2014/0094691 to Steinberg, and/or WO 13/175472 to Steinberg, which are incorporated herein by reference.

As described hereinabove, typically, there is a first portion of extraluminal images belonging to the sequence of extraluminal images for which the locations of the endoluminal device within the images are mapped to the roadmap image. The computer processor determines the locations of endoluminal data sets that were acquired at the same time as such images were acquired, with respect to the roadmap image, based upon the mapping. Locations of additional endoluminal data sets with respect to the roadmap image are typically determined using interpolation techniques. Thus, typically, processor 28 determines the locations of a first portion of the endoluminal data sets with respect to the roadmap image by mapping between the corresponding extraluminal images and the roadmap image. In addition, the processor determines locations of a second portion of the endoluminal data sets with respect to the roadmap image, using interpolation techniques.

For some applications, in step 68 of FIG. 2, computer processor 28 only shows the correspondence between the first portion of the endoluminal data sets and locations within the roadmap image. For example, in response to an input from a user (e.g., via user interface 30), the processor may only show the correspondence between the first portion of the endoluminal data sets and locations within the roadmap image. Alternatively or additionally, the processor may generate a stack of endoluminal data sets (e.g., an endoluminal image stack) using only endoluminal data sets belonging to the first portion of endoluminal data sets.

For some applications, the processor shows the correspondence between both the first and second portions of endoluminal data sets and locations within the roadmap image, and/or generates a stack of endoluminal data sets using endoluminal data sets belonging to both of the first and second portions of endoluminal data sets. In addition, the processor generates an indication of which of the endoluminal data sets belong to the first portion of endoluminal data sets, and which of the endoluminal data sets belong to the second portion of endoluminal data sets, e.g., using a color scheme, or an alternative graphical feature to differentiate between endoluminal data sets belonging to the first and second portions of endoluminal data sets.

It is noted that although some techniques described herein are described primarily with respect to extraluminal fluoroscopic/angiographic images, the scope of the present invention includes applying the techniques described herein to other forms of extraluminal images, mutatis mutandis.

Although some techniques described herein are described primarily as being performed on a blood vessel, the scope of the present application includes performing similar techniques on a lumen in the vascular system, the respiratory tract, the digestive tract, the urinary tract, any other luminal structure within a subject's body, or any other suitable anatomical structure within a subject's body, mutatis mutandis. Examples of an anatomical structure to which the techniques described herein may be applied include a coronary vessel, a coronary lesion, a vessel, a vascular lesion, a lumen, a luminal lesion, and/or a valve.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer-readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer usable or computer readable medium is a non-transitory computer usable or computer readable medium.

Examples of a computer readable medium include a semiconductor or solid state memory, magnetic tape, a removable computer diskette, a random access memory (RAM), a read-only memory (ROM), a rigid magnetic disk, and an optical disk. Examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem, and Ethernet cards are just a few of the currently available types of network adapters.

Computer program code for carrying out operations of the present invention may be written in any combination of one or more programming languages, including an object-oriented programming language such as Java, Smalltalk, C++ or the like, and conventional procedural programming languages, such as the C programming language or similar programming languages.

It will be understood that each block of the flowcharts shown in FIGS. 2 and 4 and combinations of blocks in the flowchart, can be implemented by computer program instructions. These computer program instructions may be provided to a processor of a general-purpose computer, special-purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data-processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special-purpose computer. For example, when programmed to perform the algorithms described with reference to FIGS. 2 and 4, computer processor 28 typically acts as a special-purpose image-mapping computer processor. Typically, the operations described herein that are performed by computer processor 28 transform the physical state of memory 29, which is a real physical article, to have a different magnetic polarity, electrical charge, or the like depending on the technology of the memory that is used.

In accordance with some applications, a first extraluminal image of a lumen of a subject's body is designated as a roadmap image. For example, the roadmap image may be an image of a blood vessel of the subject (e.g., a coronary artery) acquired using angiographic imaging. For some applications, the computer processor designates the extraluminal image by selecting one extraluminal image from a set of extraluminal images (e.g., a set of angiographic images) as the roadmap image. The computer processor identifies a set of pixels within the roadmap image that are indicative of a shape of the lumen within the roadmap image. For example, the lumen may be visible within the roadmap image, and the computer processor may identify a set of pixels that corresponds to a center-line of the lumen, based upon the visible lumen.

While an endoluminal device moves along a portion of the lumen, a sequence of extraluminal images of the endoluminal device inside the lumen is acquired, using an extraluminal imaging device. For example, a fluoroscopic image sequence may be acquired while an intravascular ultrasound probe is pulled back through the lumen. For each of at least a portion of the images belonging to the sequence of extraluminal images, the following steps are performed with respect to each of at least some of the pixels within the image: (1) the closest pixel to the pixel from the set of pixels within the roadmap image is identified, and (2) the distance between the pixel and the pixel identified as the closest pixel to the pixel is calculated.

At least partially in response to performing the above-described steps with respect to some of the pixels within the images belonging to the sequence of extraluminal images, a method is selected for identifying, with respect to the roadmap image, a location at which the endoluminal device was located at a time at which the image belonging to the sequence of extraluminal images was acquired. For example, based upon the distances between the pixels in the image belonging to the sequence of images and the pixels identified as the closest pixels to the pixels from the set of pixels within the roadmap image, a level of similarity between the image belonging to the sequence of images and the roadmap image may be determined. The level of similarity may then be used an input for selecting whether to (a) map the location of the endoluminal device within the image belonging to the sequence of extraluminal images to a corresponding location within the roadmap image, or (b) to determine the location of the endoluminal device with respect to the roadmap image, by interpolating between locations of the endoluminal device within the roadmap image at times at which different extraluminal images were acquired.

The selected method (e.g., method (a) or (b) described in the previous paragraph) is typically used to identify the location of the endoluminal device at the time that the image was acquired, with respect to the roadmap image. Typically, the above-described steps are performed with respect to a plurality of extraluminal images belonging to the sequence of extraluminal images, the plurality of images having been acquired at respective times during movement of the endoluminal device through the lumen. Thus, the computer processor determines the location of the endoluminal device with respect to the roadmap image at times corresponding to the acquisitions of a plurality of images belonging to the sequence of extraluminal images, the images having been acquired at respective times during the movement of the endoluminal device through the lumen. At least partially in response thereto, the computer processor generates an output on an output device.

Typically, the previously described step, of identifying the closest pixels from the set of pixels within the roadmap image to pixels belonging to images belonging to the sequence of images, is performed with respect to one or more pixels within images belonging to the sequence of extraluminal images that correspond to a portion of the endoluminal device. For some such applications, if method (a) is selected, then the mapping is performed by mapping the location of the endoluminal device within the image belonging to the sequence of extraluminal images to the pixel that was previously determined as being closest to the pixel from the set of pixels within the roadmap image.

For some applications, the endoluminal device includes an endoluminal data acquisition device configured to acquire a plurality of endoluminal data sets, from respective locations along the lumen (e.g., an endoluminal imaging device that is configured to acquire a plurality of endoluminal images, or an endoluminal data-acquisition device that is configured to acquire a plurality of functional endoluminal data sets). Based upon determining the locations of the endoluminal device times at which respective images belonging to the sequence of extraluminal images were acquired, with respect to the roadmap image, the computer processor determines the locations within the lumen at which respective endoluminal data sets were acquired by the endoluminal data-acquisition device. Based upon the determined locations within the lumen at which the endoluminal data sets were acquired, the computer processor may generate an output, such as by generating an endoluminal image stack, and/or by generating an indication of the correspondence between an endoluminal data set and the location within the lumen at which the endoluminal data set was acquired. Alternatively, based upon the determined locations within the lumen at which the endoluminal data sets were acquired, the computer processor may co-use endoluminal data sets and extraluminal imaging using techniques described herein, and/or as described in US 2012/0004537 to Tolkowsky, US 2014/0094691 to Steinberg, and/or WO 13/175472 to Steinberg, which are incorporated herein by reference.

There is therefore provided, in accordance with some applications of the present invention, a method including:

designating an extraluminal image of a lumen of a body of a subject as a roadmap image;

identifying a set of pixels within the roadmap image as being indicative of a shape of the lumen within the roadmap image;

while an endoluminal device moves along a portion of the lumen, acquiring a sequence of extraluminal images of the endoluminal device inside the lumen, using an extraluminal imaging device;

using at least one computer processor, for each of at least a portion of the images belonging to the sequence of extraluminal images:
for each of at least some of the pixels within the image:
identifying the closest pixel to the pixel from the set of pixels within the roadmap image; and
calculating a distance between the pixel and the pixel from the set of pixels within the roadmap image that is identified as the closest pixel;
at least partially in response thereto, selecting a method for identifying, with respect to the roadmap image, a location at which the endoluminal device was located at a time at which the image belonging to the sequence of extraluminal images was acquired; and
using the selected method, identifying the location with respect to the roadmap image; and
at least partially in response thereto, generating an output on an output device.

In some applications, generating the output includes generating an indication of which method was used to identify at least one of the locations of the endoluminal device.

In some applications, designating the first extraluminal image of the lumen of the subject's body as the roadmap image, includes using the at least one computer processor to designate the first extraluminal image of the lumen of the subject's body as the roadmap image.

In some applications, identifying the set of pixels within the roadmap image as being indicative of the shape of the lumen within the roadmap image includes using the at least one computer processor to identify the set of pixels within the roadmap image as being indicative of the shape of the lumen within the roadmap image.

In some applications,
the method further includes accounting for a change in a position of the subject's body between an acquisition of the roadmap image, and the acquiring of the sequence of extraluminal images,
for at least some of the pixels within the image belonging to the sequence of images, identifying the closest pixel to the pixel from the set of pixels within the roadmap image includes accounting for the change in the position of the subject's body, and
for at least some of the pixels within the image belonging to the sequence of images, calculating the distance between the pixel and the pixel identified as the closest pixel includes accounting for the change in the position of the subject's body.

In some applications, for at least some of the pixels within the image, identifying the closest pixel to the pixel from the set of pixels within the roadmap image includes:
identifying pixels within the image belonging to the sequence of extraluminal images that correspond to visible features within the image; and
for each of the identified pixels, identifying the closest pixel to the pixel from the set of pixels within the roadmap image.

In some applications,
the method further includes determining a function that describes, for each of a plurality of pixels within a master image, the closest pixel to the pixel from the set of pixels within the roadmap image and a distance between the pixel and the pixel from the set of pixels within the roadmap image that is identified as the closest pixel,
for at least some of the pixels within the image belonging to the sequence of images, identifying the closest pixel to the pixel from the set of pixels within the roadmap image includes using the function determined for the master image, and
for at least some of the pixels within the image belonging to the sequence of images, calculating a distance between the pixel and the pixel identified as the closest pixel includes using the function determined for the master image.

In some applications, selecting the method for identifying, with respect to the roadmap image, the location at which the endoluminal device was located at a time at which the image belonging to the sequence of extraluminal images was acquired includes:
at least partially based upon the distances between the pixels in the image belonging to the sequence of images and the pixels identified as the closest pixels to the pixels from the set of pixels within the roadmap image, determining a level of similarity between the image belonging to the sequence of images and the roadmap image;
at least partially based on the level of similarity, selecting whether to identify, with respect to the roadmap image, the location at which the endoluminal device was located at a time at which the image belonging to the sequence of extraluminal images was acquired by:
mapping the location of the endoluminal device within the image belonging to the sequence of extraluminal images to a corresponding location within the roadmap image, or
interpolating between locations of the endoluminal device within the roadmap image.

In some applications:
for at least some of the pixels within the image, identifying the closest pixel to the pixel from the set of pixels within the roadmap image includes:
identifying a pixel within the image belonging to the sequence of images as corresponding to a portion of the endoluminal device; and
identifying the closest pixel to the identified pixel from the set of pixels within the roadmap image; and
identifying the location with respect to the roadmap image includes:
in response to selecting to identify the location by mapping the location of the endoluminal device within the image belonging to the sequence of extraluminal images to the corresponding location within the roadmap image,
performing the mapping by mapping the pixel corresponding to the portion of the endoluminal device within the image belonging to the sequence of images to the pixel from the set of pixels within the roadmap image that was identified as being the closest pixel.

In some applications,
the endoluminal device includes an endoluminal data-acquisition device configured to acquire a plurality of endoluminal data sets from respective longitudinal locations along the lumen, while the endoluminal data-acquisition device moves along the portion of the lumen,
the method further including, based upon determining locations at which the endoluminal device was located at times at which the respective extraluminal images belonging to the sequence of extraluminal images were acquired, co-registering respective endoluminal data sets to respective locations within the roadmap image, and
generating the output includes generating an output based upon the co-registration of the endoluminal data sets to the respective locations within the roadmap image.

In some applications, the endoluminal data-acquisition device includes an endoluminal imaging device that is configured to acquire a plurality of endoluminal images while the endoluminal imaging device moves along the portion of the lumen, and co-registering respective endoluminal data sets to respective locations within the roadmap image includes co-registering respective endoluminal images to respective locations within the roadmap image.

In some applications, the endoluminal data-acquisition device includes an endoluminal data-acquisition device that is configured to acquire functional data regarding the lumen, while the endoluminal data-acquisition device moves along the portion of the lumen, and co-registering respective endoluminal data sets to respective locations within the roadmap image includes co-registering respective functional endoluminal data sets to respective locations within the roadmap image.

In some applications, generating the output based upon the co-registration includes generating a stack of endoluminal data sets, in which relative dispositions of endoluminal data sets within the stack correspond to relative locations of the endoluminal data sets within the roadmap image.

There is further provided, in accordance with some applications of the present invention, apparatus including:
an endoluminal device configured to move along a portion of the lumen of a body of a subject;
one or more extraluminal imaging devices configured to acquire a sequence of extraluminal images of the endoluminal device inside the lumen, while the endoluminal device moves along the portion of the lumen;
an output device; and
at least one computer processor configured to:
designate an extraluminal image of the lumen as a roadmap image;
identify a set of pixels within the roadmap image as being indicative of a shape of the lumen within the roadmap image;
for each of at least a portion of the images belonging to the sequence of extraluminal images:
for each of at least some of the pixels within the image:
identify the closest pixel to the pixel from the set of pixels within the roadmap image; and
calculate a distance between the pixel and the pixel from the set of pixels within the roadmap image that is identified as the closest pixel;
at least partially in response thereto, select a method for identifying, with respect to the roadmap image, a location at which the endoluminal device was located at a time at which the image belonging to the sequence of extraluminal images was acquired; and
using the selected method, identify the location with respect to the roadmap image; and
at least partially in response thereto, generate an output on an output device.

In some applications, the computer processor is configured to generate the output by generating an output that includes an indication of which method was used to identify at least one of the locations of the endoluminal device.

In some applications, the at least one computer processor is configured to designate the first one of the extraluminal images of the lumen as the roadmap image, at least partially in response to an input from a user.

In some applications, the at least one computer processor is configured to identify the set of pixels within the roadmap image as being indicative of the shape of the lumen within the roadmap image, at least partially in response to an input from a user.

In some applications, the at least one computer processor is configured:
to account for a change in a position of the subject's body between an acquisition of the roadmap image, and the acquiring of the sequence of extraluminal images,
for at least some of the pixels within the image belonging to the sequence of images, to identify identifying the closest pixel to the pixel from the set of pixels within the roadmap image by accounting for the change in the position of the subject's body, and
for at least some of the pixels within the image belonging to the sequence of images, to calculate the distance between the pixel and the pixel identified as the closest pixel by accounting for the change in the position of the subject's body.

In some applications, the at least one computer processor is configured, for at least some of the pixels within the image, to identify the closest pixel to the pixel from the set of pixels within the roadmap image by:
identifying pixels within the image belonging to the sequence of extraluminal images that correspond to visible features within the image; and
for each of the identified pixels, identifying the closest pixel to the pixel from the set of pixels within the roadmap image.

In some applications, the at least one computer processor is configured:
to determine a function that describes for each of a plurality of pixels within a master image, the closest pixel to the pixel from the set of pixels within the roadmap image and a distance between the pixel and the pixel from the set of pixels within the roadmap image that is identified as the closest pixel,
for at least some of the pixels within the image belonging to the sequence of images, to identify the closest pixel to the pixel from the set of pixels within the roadmap image by using the function determined for the master image, and
for at least some of the pixels within the image belonging to the sequence of images, to calculate a distance between the pixel and the pixel identified as the closest pixel by using the function determined for the master image.

In some applications, the at least one computer processor is configured to select the method for identifying, with respect to the roadmap image, the location at which the endoluminal device was located at a time at which the image belonging to the sequence of extraluminal images was acquired by:
at least partially based upon the distances between the pixels in the image belonging to the sequence of images and the pixels identified as the closest pixels to the pixels from the set of pixels within the roadmap image, determining a level of similarity between the image belonging to the sequence of images and the roadmap image;
at least partially based on the level of similarity, selecting whether to identify, with respect to the roadmap image, the location at which the endoluminal device was located at a time at which the image belonging to the sequence of extraluminal images was acquired by:
mapping the location of the endoluminal device within the image belonging to the sequence of extraluminal images to a corresponding location within the roadmap image, or
interpolating between locations of the endoluminal device within the roadmap image.

In some applications,
the at least one computer processor is configured, when identifying, for each of at least some of the pixels within the image, the closest pixel to the pixel from the set of pixels within the roadmap image, to:
  identify a pixel within the image belonging to the sequence of images as corresponding to a portion of the endoluminal device; and
  identify the closest pixel to the identified pixel from the set of pixels within the roadmap image; and
the at least one computer processor is configured to identify the location with respect to the roadmap image by:
  in response to selecting to identify the location by mapping the location of the endoluminal device within the image belonging to the sequence of extraluminal images to the corresponding location within the roadmap image,
  performing the mapping by mapping the pixel corresponding to the portion of the endoluminal device within the image belonging to the sequence of images to the pixel from the set of pixels within the roadmap image that was identified as being the closest pixel.

In some applications,
the endoluminal device comprises an endoluminal data-acquisition device configured to acquire a plurality of endoluminal data sets from respective longitudinal locations along the lumen, while the endoluminal data-acquisition device moves along the portion of the lumen,
the at least one computer processor is configured, based upon determining locations at which the endoluminal device was located at times at which the respective extraluminal images belonging to the sequence of extraluminal images were acquired, to co-register respective endoluminal data sets to respective locations within the roadmap image, and
the at least one computer processor is configured to generate the output by generating an output based upon the co-registration of the endoluminal data sets to the respective locations within the roadmap image.

In some applications, the endoluminal data-acquisition device includes an endoluminal imaging device that is configured to acquire a plurality of endoluminal images while the endoluminal imaging device moves along the portion of the lumen, and the at least one computer processor is configured to co-register respective endoluminal data sets to respective locations within the roadmap image by co-registering respective endoluminal images to respective locations within the roadmap image.

In some applications, the endoluminal data-acquisition device includes an endoluminal data-acquisition device that is configured to acquire functional data regarding the lumen, while the endoluminal data-acquisition device moves along the portion of the lumen, and the at least one computer processor is configured to co-register respective endoluminal data sets to respective locations within the roadmap image by co-registering respective functional endoluminal data sets to respective locations within the roadmap image.

In some applications, the at least one computer processor is configured to generate the output based upon the co-registration by generating a stack of endoluminal data sets, in which relative dispositions of endoluminal data sets within the stack correspond to relative locations of the endoluminal data sets within the roadmap image.

There is further provided, in accordance with some applications of the present invention, a computer software product, for use with an endoluminal device that is configured to move along a portion of a lumen of a subject, one or more extraluminal imaging devices configured to acquire a sequence of extraluminal images of the endoluminal device inside the lumen, while the endoluminal device moves along the portion of the lumen, and an output device, the computer software product including a non-transitory computer-readable medium in which program instructions are stored, which instructions, when read by a computer cause the computer to perform the steps of: designating an extraluminal image of the lumen as a roadmap image; identifying a set of pixels within the roadmap image as being indicative of a shape of the lumen within the roadmap image; for each of at least a portion of the images belonging to the sequence of extraluminal images: for each of at least some of the pixels within the image: identifying the closest pixel to the pixel from the set of pixels within the roadmap image; and calculating a distance between the pixel and the pixel from the set of pixels within the roadmap image that is identified as the closest pixel; at least partially in response thereto, selecting a method for identifying, with respect to the roadmap image, a location at which the endoluminal device was located at a time at which the image belonging to the sequence of extraluminal images was acquired; and, using the selected method, identifying the location with respect to the roadmap image; and, at least partially in response thereto, generating an output on an output device.

There is further provided, in accordance with some applications of the present invention, a method including:
designating an extraluminal image of a lumen of a body of a subject as a roadmap image;
identifying a set of pixels within the roadmap image as being indicative of a shape of the lumen within the roadmap image;
while an endoluminal device moves along a portion of the lumen, acquiring a sequence of extraluminal images of the endoluminal device inside the lumen, using an extraluminal imaging device; and
using at least one computer processor:
  for each of at least a portion of the images belonging to the sequence of extraluminal images:
    selecting, from a choice of methods, a method for identifying, with respect to the roadmap image, a location at which the endoluminal device was located at a time at which the image belonging to the sequence of extraluminal images was acquired; and
    using the selected method, identifying the location with respect to the roadmap image; and
  at least partially in response thereto, generating an output on an output device, the output including an indication of which method was used to identify at least one of the locations of the endoluminal device.

There is further provided, in accordance with some applications of the present invention, a method including:
displaying an extraluminal image of a lumen of a body of a subject in which a first indication of a location of the lumen is shown, while an endoluminal device moves along a portion of a lumen of a body of a subject;
acquiring a sequence of extraluminal images of the endoluminal device moving along the portion of the lumen, using an extraluminal imaging device;
updating the indication of the location of the lumen that is displayed, based upon the acquired sequence of extraluminal images of the endoluminal device moving along the portion of the lumen; and
displaying the sequence of images of the endoluminal device moving along the portion of the lumen with the updated indication of the location of the lumen overlaid upon the images.

In some applications, the method further includes displaying the sequence of images of the endoluminal device moving along the portion of the lumen with the first indication of the location of the lumen overlaid upon the images.

In some applications, based upon the sequence of images that were acquired while the endoluminal device moved along the lumen updating the indication of the location of the lumen that is displayed includes:

identifying, within the acquired extraluminal sequence of images, locations at which visible features were imaged within the sequence of extraluminal images;

defining a set of locations at which the visible features were located over the course of the sequence of extraluminal images, based upon the identified locations; and determining an updated location of the lumen, based upon the set of locations.

In some applications, defining the set of locations at which the visible features were located over the course of the sequence of extraluminal images includes generating a combined image in which the identified locations at which visible features were imaged within the acquired sequence of extraluminal images form an integrated set of locations, by overlaying, upon each other, the locations of the visible features identified in each of the images belonging to the sequence of acquired extraluminal images.

In some applications, the endoluminal device includes an endoluminal data-acquisition device configured to acquire a plurality of endoluminal data sets from respective longitudinal locations along the lumen, while the endoluminal data-acquisition device moves along the portion of the lumen, and the method further includes co-registering respective endoluminal data sets to respective locations along the lumen.

In some applications, the endoluminal data-acquisition device includes an endoluminal imaging device that is configured to acquire a plurality of endoluminal images while the endoluminal imaging device moves along the portion of the lumen, and co-registering respective endoluminal data sets to respective locations along the lumen includes co-registering respective endoluminal images to respective locations along the lumen.

In some applications, the endoluminal data-acquisition device includes an endoluminal data-acquisition device that is configured to acquire functional data regarding the lumen, while the endoluminal data-acquisition device moves along the portion of the lumen, and co-registering respective endoluminal data sets to respective locations along the lumen includes co-registering respective functional endoluminal data sets to respective locations along the lumen.

In some applications, the method further includes displaying a plot in which the endoluminal data sets are plotted against a distance along the lumen at which the data sets were acquired.

In some applications, the method further includes:

while displaying the sequence of images of the endoluminal device moving along the portion of the lumen with the updated indication of the location of the lumen overlaid upon the images, displaying an icon on the plot that is indicative of the location of the endoluminal data-acquisition device that is currently being shown in the sequence of images, with respect to the plot.

There is further provided, in accordance with some applications of the present invention, apparatus including:

at least one display;

an endoluminal device configured to move along a portion of a lumen of a body of a subject;

an extraluminal imaging device; and at least one computer processor configured to:

drive the display to display an extraluminal image of the lumen in which a first indication of a location of the lumen is shown, while the endoluminal device moves along the portion of the lumen;

drive the extraluminal imaging device to acquire a sequence of extraluminal images of the endoluminal device moving along the portion of the lumen;

drive the display to update the indication of the location of the lumen that is displayed, based upon the acquired sequence of extraluminal images of the endoluminal device moving along the portion of the lumen; and drive the display to display the sequence of images of the endoluminal device moving along the portion of the lumen with the updated indication of the location of the lumen overlaid upon the images.

In some applications, the computer processor is further configured to drive the at least one display to display the sequence of images of the endoluminal device moving along the portion of the lumen with the first indication of the location of the lumen overlaid upon the images.

In some applications, the computer processor is configured to determine an updated location of the lumen by:

identifying, within the acquired extraluminal sequence of images, locations at which visible features were imaged within the sequence of extraluminal images;

defining a set of locations at which the visible features were located over the course of the sequence of extraluminal images, based upon the identified locations; and determining the updated location of the lumen, based upon the set of locations.

In some applications, the computer processor is configured to define the set of locations at which the visible features were located over the course of the sequence of extraluminal images by generating a combined image in which the identified locations at which visible features were imaged within the acquired sequence of extraluminal images form an integrated set of locations, by overlaying, upon each other, the locations of the visible features identified in each of the images belonging to the sequence of acquired extraluminal images.

In some applications, the endoluminal device comprises an endoluminal data-acquisition device configured to acquire a plurality of endoluminal data sets from respective longitudinal locations along the lumen, while the endoluminal data-acquisition device moves along the portion of the lumen, and the computer processor is further configured to co-register respective endoluminal data sets to respective locations along the lumen.

In some applications, the endoluminal data-acquisition device includes an endoluminal imaging device that is configured to acquire a plurality of endoluminal images while the endoluminal imaging device moves along the portion of the lumen, and the computer processor is configured to co-register respective endoluminal data sets to respective locations along the lumen by co-registering respective endoluminal images to respective locations along the lumen.

In some applications, the endoluminal data-acquisition device includes an endoluminal data-acquisition device that is configured to acquire functional data regarding the lumen, while the endoluminal data-acquisition device moves along the portion of the lumen, and the computer processor is configured to co-register respective endoluminal data sets to respective locations along the lumen by co-registering respective functional endoluminal data sets to respective locations along the lumen.

In some applications, the computer processor is further configured to drive the at least one display to display a plot in which the endoluminal data sets are plotted against a distance along the lumen at which the data sets were acquired.

In some applications, the computer processor is further configured:

while the display is displaying the sequence of images of the endoluminal device moving along the portion of the lumen with the updated indication of the location of the lumen overlaid upon the images, to drive the display to display an icon on the plot that is indicative of the location of the endoluminal data-acquisition device that is currently being shown in the sequence of images, with respect to the plot.

There is further provided, in accordance with some applications of the present invention, a computer software product, for use with an endoluminal device that is configured to move along a portion of a lumen of a subject, the computer software product including a non-transitory computer-readable medium in which program instructions are stored, which instructions, when read by a computer cause the computer to perform the steps of: displaying an extraluminal image of the lumen in which a first indication of a location of the lumen is shown, while the endoluminal device moves along the portion of the lumen; acquiring a sequence of extraluminal images of the endoluminal device moving along the portion of the lumen, using an extraluminal imaging device; updating the indication of the location of the lumen that is displayed, based upon the acquired sequence of extraluminal images of the endoluminal device moving along the portion of lumen; and displaying the sequence of images of the endoluminal device moving along the portion of the lumen with the updated indication of the location of the lumen overlaid upon the images.

The scope of the present application includes combining the apparatus and methods described herein with apparatus and methods described in any one of the following applications, all of which are incorporated herein by reference:

International Application PCT/IL2008/000316 to Iddan (published as WO 08/107905), filed Mar. 9, 2008, entitled "Imaging and tools for use with moving organs."

U.S. patent application Ser. No. 12/075,252 to Iddan (published as US 2008/0221440), filed Mar. 10, 2008, entitled "Imaging and tools for use with moving organs;"

International Application PCT/IL2009/000610 to Iddan (published as WO 09/153794), filed Jun. 18, 2009, entitled "Stepwise advancement of a medical tool;"

U.S. patent application Ser. No. 12/487,315 to Iddan (issued as U.S. Pat. No. 8,700,130), filed Jun. 18, 2009, entitled "Stepwise advancement of a medical tool;"

U.S. patent application Ser. No. 12/666,879 to Steinberg (issued as U.S. Pat. No. 8,781,193), which is the US national phase of PCT Application No. PCT/IL2009/001089 to Cohen (published as WO 10/058398), filed Nov. 18, 2009, entitled "Image processing and tool actuation for medical procedures;"

U.S. patent application Ser. No. 12/781,366 to Cohen (published as US 2010/0222671), filed May 17, 2010, entitled "Identification and presentation of device-to-vessel relative motion;"

International Patent Application PCT/IL2011/000391 to Cohen (published as WO 11/145094), filed May 17, 2011, entitled "Identification and presentation of device-to-vessel relative motion;"

U.S. Ser. No. 13/228,229 to Tolkowsky (published as US 2012/0004537), filed Sep. 8, 2011, which is a continuation of International Application No. PCT/IL2011/000612 to Tolkowsky (published as WO 12/014212), filed 28 Jul. 2011 entitled "Co-use of endoluminal data and extraluminal imaging;"

U.S. patent application Ser. No. 14/128,243 to Barzelay (published as US 2014/0140597), which is the US national phase of International Patent Application PCT/IL2012/000246 (published as WO 12/176191), filed Jun. 21, 2012, entitled "Luminal background cleaning;"

U.S. patent application Ser. No. 14/097,922 to Steinberg (published as US 2014/0094691), filed Dec. 5, 2013, entitled "Co-use of endoluminal data and extraluminal imaging," which is a continuation of International Application PCT/IL2013/050438 (published as WO 13/175472) to Steinberg, filed May 21, 2013, entitled "Co-use of endoluminal data and extraluminal imaging;"

U.S. patent application Ser. No. 14/142,082 to Tolkowsky (published as US 2014/0121513), filed Dec. 27, 2013, entitled "Determining a characteristic of a lumen by measuring velocity of a contrast agent," which is a continuation of International Application PCT/IL2013/050549 (published as WO 14/002095) to Tolkowsky, filed Jun. 26, 2013, entitled "Flow-related image processing in luminal organs;"

International Patent Application PCT/IL2015/050372 to Klaiman (published as WO 15/155770), filed Apr. 2, 2015, entitled "Image analysis in the presence of a medical device," which claims priority from U.S. Provisional Patent Application 61/977,891 to Klaiman, filed Apr. 10, 2014, entitled "Image analysis in the presence of a medical device;" and International Patent Application PCT/IL2015/050509 to Klaiman (published as WO 15/173821), filed May 13, 2015, entitled "Object identification," which claims priority from U.S. Provisional Patent Application 61/993,123 to Klaiman, filed May 14, 2014, entitled "Image analysis in the presence of a medical device."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   at least one computer processor configured for communication with an extraluminal imaging device and a display, wherein the at least one computer processor is configured to:
   drive the display to display an extraluminal roadmap image of a lumen of a body of a subject, the extraluminal roadmap image showing a pathway of the lumen, wherein the extraluminal roadmap image is obtained with a contrast agent within the lumen;
   identify, in the extraluminal roadmap image, a plurality of first pixels comprising the pathway of the lumen;
   acquire, using the extraluminal imaging device, a sequence of extraluminal images of an endoluminal device moving along the lumen, wherein the sequence of extraluminal images is obtained without the contrast agent within the lumen;

select a master image comprising a plurality of second pixels, wherein the master image comprises an extraluminal image in the sequence of extraluminal images or a blank image with a size corresponding to a size of the extraluminal image in the sequence of extraluminal images;

determine a closest pixel of the plurality of second pixels to a pixel of the plurality of first pixels;

determine a distance between the closest pixel of the plurality of second pixels and the pixel of the plurality of first pixels;

for each extraluminal image in the sequence of extraluminal images:
  identify, in a respective extraluminal image, a selected pixel that includes the endoluminal device; and
  map the selected pixel that includes the endoluminal device to the closet pixel of the plurality of second pixels;

determine, for each extraluminal image in the sequence of extraluminal images, a location of the endoluminal device on the pathway of the lumen, based on the mapping, while the endoluminal device moves along the lumen; and drive the display to display, on the extraluminal roadmap image, an output indicative of the determined locations of the endoluminal device on the pathway of the lumen while the endoluminal device moves along the lumen.

2. The apparatus according to claim 1, wherein the at least one computer processor is further configured to drive the display to display the sequence of extraluminal images of the endoluminal device moving along the lumen with the pathway of the lumen overlaid upon extraluminal images in the sequence of extraluminal images.

3. The apparatus according to claim 1, wherein the at least one computer processor is configured to determine an updated pathway of the lumen by:
  identifying, within the sequence of extraluminal images, locations at which visible features were imaged within the sequence of extraluminal images;
  defining a set of locations at which the visible features were located in the sequence of extraluminal images, based upon the identified locations; and
  determining the updated pathway of the lumen, based upon the set of locations.

4. The apparatus according to claim 3, wherein the at least one computer processor is configured to define the set of locations at which the visible features were located in the sequence of extraluminal images by generating a combined image in which the identified locations at which visible features were imaged within the sequence of extraluminal images form an integrated set of locations, by overlaying, upon each other, the locations of the visible features identified in each of the images belonging to the sequence of extraluminal images.

5. The apparatus according to claim 1, further comprising:
  the endoluminal device,
  wherein the endoluminal device comprises an endoluminal data-acquisition device configured to acquire a plurality of endoluminal data sets from respective longitudinal locations along the lumen while the endoluminal data-acquisition device moves along the lumen, and
  wherein the at least one computer processor is further configured to co-register respective endoluminal data sets to the respective longitudinal locations along the lumen.

6. The apparatus according to claim 5,
  wherein the endoluminal data-acquisition device comprises an endoluminal imaging device that is configured to acquire a plurality of endoluminal images while the endoluminal imaging device moves along the lumen, and
  wherein the at least one computer processor is configured to co-register respective endoluminal data sets to the respective longitudinal locations along the lumen by co-registering respective endoluminal images to the respective longitudinal locations along the lumen.

7. The apparatus according to claim 5,
  wherein the endoluminal data-acquisition device is configured to acquire functional data regarding the lumen while the endoluminal data-acquisition device moves along of the lumen, and
  wherein the at least one computer processor is configured to co-register respective endoluminal data sets to the respective longitudinal locations along the lumen by co-registering respective functional endoluminal data sets to the respective longitudinal locations along the lumen.

8. The apparatus according to claim 5, wherein the at least one computer processor is further configured to drive the display to display a plot in which the endoluminal data sets are plotted against a distance along the lumen at which the data sets were acquired.

9. The apparatus according to claim 3, wherein the at least one computer processor is further configured to:
  display the sequence of extraluminal images of the endoluminal device moving along the lumen with the updated pathway of the lumen overlaid upon extraluminal images in the sequence of extraluminal images; and
  drive the display to display an icon on a plot that is indicative of a location of the endoluminal device that is currently being shown in the sequence of extraluminal images.

10. A method, comprising:
  displaying an extraluminal roadmap image of a lumen of a body of a subject, the extraluminal roadmap image showing a pathway of the lumen, wherein the extraluminal roadmap image is obtained with a contrast agent within the lumen;
  identifying, in the extraluminal roadmap image, a plurality of first pixels comprising the pathway of the lumen;
  acquiring a sequence of extraluminal images of an endoluminal device moving along the lumen, using an extraluminal imaging device, wherein the sequence of extraluminal images is obtained without the contrast agent within the lumen;
  selecting a master image comprising a plurality of second pixels, wherein the master image comprises an extraluminal image in the sequence of extraluminal images or a blank image with a size corresponding to a size of the extraluminal image in the sequence of extraluminal images;
  determining a closest pixel of the plurality of second pixels to a pixel of the plurality of first pixels;
  determining a distance between the closest pixel of the plurality of second pixels and the pixel of the plurality of first pixels;

for each extraluminal image in the sequence of extraluminal images:
identifying, in a respective extraluminal image, a selected pixel that includes the endoluminal device; and
mapping the selected pixel that includes the endoluminal device to the closet pixel of the plurality of second pixels;
determining, for each extraluminal image in the sequence of extraluminal images, a location of the endoluminal device on the pathway of the lumen, based on the mapping, while the endoluminal device moves along the lumen; and
displaying, on the extraluminal roadmap image, an output indicative of a location of the endoluminal device on the pathway of the lumen while the endoluminal device moves along the lumen.

11. The apparatus according to claim 1, wherein the at least one computer processor is further configured to change the pathway of the lumen on the extraluminal roadmap image, based upon the acquired sequence of extraluminal images of the endoluminal device moving along the lumen.

12. The apparatus according to claim 1, wherein the extraluminal roadmap image and the sequence of extraluminal images include a same pixel area of the body of the subject.

* * * * *